United States Patent [19]

Karrer

[11] 4,064,269
[45] Dec. 20, 1977

[54] 4-[(4-PHENOXY AND BENZYL)-PHENOXY]-BUTYRIC ACID ESTERS

[75] Inventor: Friedrich Karrer, Basel, Switzerland

[73] Assignee: Ciba-Geigy Corporation, Ardsley, N.Y.

[21] Appl. No.: 517,331

[22] Filed: Oct. 23, 1974

[30] Foreign Application Priority Data

Oct. 25, 1973 Switzerland .............. 15044/73
Oct. 3, 1974 Switzerland .............. 13317/74

[51] Int. Cl.$^2$ .................................. C07C 69/76
[52] U.S. Cl. .................. 424/308; 260/455 R; 260/465 F; 560/61; 260/559 B; 260/590 D; 260/613 R
[58] Field of Search ............. 260/473 G; 424/308

[56] References Cited

U.S. PATENT DOCUMENTS 3,493,604  2/1970  Nelson ............... 260/473 G
3,954,442  5/1976  Becker et al. ........ 260/473 G

OTHER PUBLICATIONS

Arsenescu, N., Chemical Abstracts, vol. 81, 3538q, 1974.
Wyrzykiewicz, E., Chemical Abstracts, vol. 81, 63296u, 1974.
Rodriguez-Rebollo, M., Chemical Abstracts, vol. 70, 105343n, 1969.

Primary Examiner—Paul J. Killos
Attorney, Agent, or Firm—Frederick H. Rabin

[57] ABSTRACT

New ethers of the formula

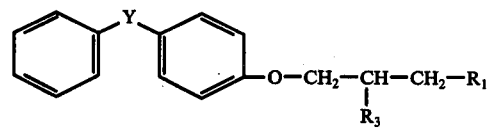

(I)

wherein
R$_1$ represents cyano or the radical

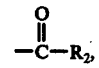

R$_2$ = methoxy, ethoxy, propoxy, isopropoxy, n-, i-, sec.-, tert.-butoxy, propargyloxy, methylthio, ethylthio, isopropylthio, methylamino, ethylamino, isopropylamino, dimethylamino, diethylamino or methyl,
R$_3$ represents hydrogen or methyl, and
Y represents — CH$_2$— or — O — their preparation and their use as pest controlling agents are disclosed.

11 Claims, No Drawings

4-[(4-PHENOXY AND BENZYL)-PHENOXY]-BUTYRIC ACID ESTERS

The present invention relates to arylalkyl ethers, to processes for their preparation and to their use in pest control.

The compound correspond to the formula

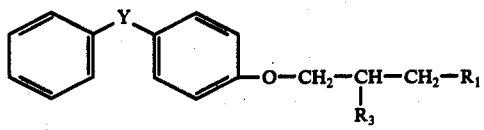
(I)

wherein
R$_1$ represents cyano or the radical

R$_2$ = methoxy, ethoxy, propoxy, ispropoxy, n-, i-, sec.-, tert.-butoxy, propargyloxy, methylthio, ethylthio, isopropylthio, methylamino, ethylamino, isopropylamino, dimethylamino, diethylamino or methyl,
R$_3$ represents hydrogen or methyl, and
Y represents —CH$_2$— or —O—.

Compounds of formula I preferred because of their action are those wherein
R$_1$ represents methoxycarbonyl, ethoxycarbonyl, isopropoxycarbonyl, N-ethylcarbamoyl, N,N-diethylcarbamoyl or acetyl,
R$_3$ represents hydrogen or methyl, and
Y represents —CH$_2$— or —O—.

The compounds of formula I can be prepared by methods known per se, e.g., as follows:

A)

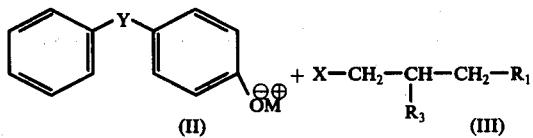

B)

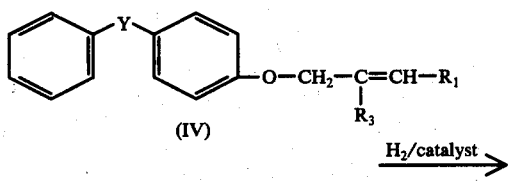

C. Variant of A for preparation of compounds of formula I wherein R$_1$ represents methyl.

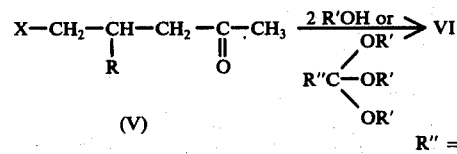

R" = H, again alkyl

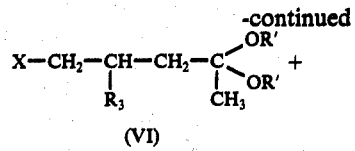

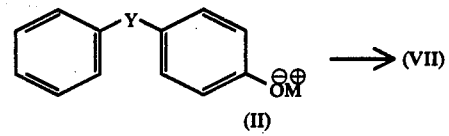

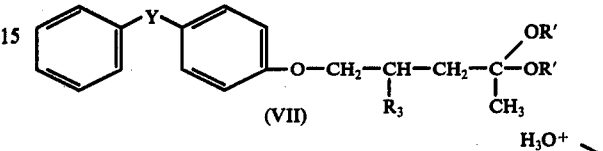

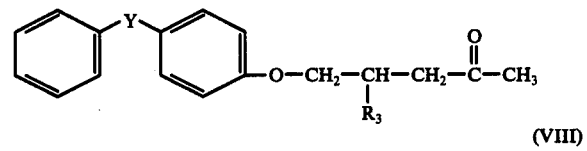

D. Variant of C for preparation of compounds of formula VIII.

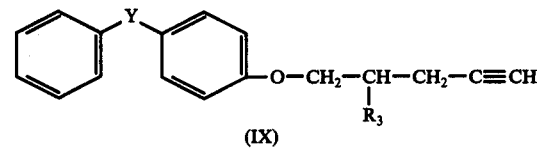

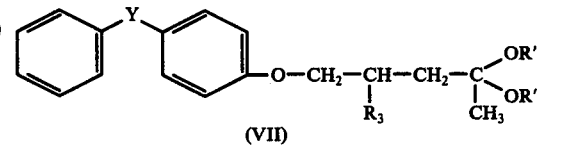

In formulae II to IX, the symbols R$_1$ to R$_3$ and Y have the meanings given for formula I, X stands for halogen, especially for chlorine or bromine, R' for C$_1$—C$_4$—alkyl and M for an alkali metal, particularly sodium or potassium.

The reactions A and C are performed at normal pressure and in solvents and diluents inert to the reactants. Suitable inert solvents and diluents are, e.g., anhydrous dimethylsulphoxide, dialkylformamides, hexamethylphosphoric acid triamide, also ethers, such as tetrahydrofuran, 1,2-dimethoxyethane, dioxane or dialkyl ether, as well as ketones, such as acetone, methyl ethyl ketone or cyclohexanone. The reaction temperatures, which are not very critical, are between 0° C and 150° C, depending on the employed solvents and on the base used; with dimethylsulphoxide in the presence of alkali hydroxides or alkali alkoxides, e.g., between 10° C and 40° C; and with dimethylformamide in the presence of an alkali carbonate, e.g., between 20° C and 140° C. Hydrogenation B is performed in the presence of a metal catalyst, such as noble metal catalyst, such as, e.g., nickel, cobalt, palladium, platinum, rhodium, ruthenium or iridium, optionally finely dispersed on a suitable carrier material, such as barium sulphate, carbon, aluminium oxide, etc., at a temperature of between 0° C and 50° C, usually at room temperature and in an inert solvent, such as dioxane, ethyl acetate, an alcohol or dimethylformamide. Starting materials of formulae II, III, IV and V are known, or can be prepared by methods analogous to known methods.

Variant C can be taken as being the preferred process for preparation of the methyl ketones of formula I.

According to this known process, a 1-halopentan-4-one derivative is firstly converted into its ketal VI, and this ketal is condensed with the desired phenolate to aryl-alkyl ether VII. Finally, the ketal grouping introduced as protective group is hydrolysed again to the methyl ketone.

The preparation of ketal VI is effected by known methods, e.g., by reaction of the ketone with a monovalent aliphatic alcohol or with a 1,2-diol in the presence of a catalytic amount of an acid, such as p-toluenesulphonic acid or a mineral acid, with azeotropic separation of water with the aid of known water-entrainers, such as chloroform, benzene, toluene, xylene, etc., or by reaction of a ketone VI with orthoformic acid trialkyl ester.

The condenstion to 5-aryloxy-pentanone-2-ketal VII is performed as described under A. The subsequent splitting to the free methyl ketone is effected by acid catalytic hydrolysis.

According to equation D, the triple bond of the pentinyloxy compound IX is converted by $Hg^{2+}$ catalysis in the presence of an alcohol R'OH into the corresponding acetol VII, which is subsequently hydrolysed with dilute acid to the ketone.

The preparation of the starting materials of formula IX is described in the German Offenlegungsschrift 2,322,853.

In J. med. Chem. 12, 911–913 (1969), it has been described how a double bond in conjugation with the carbonyl group is a decisive factor with respect to the action of juvenile hormones. Accordingly, hydrogenation of the double bond should drastically reduce the action of juvenile hormones.

It has now been found that, surprisingly, such compounds of formula I which are saturated in their side chain have a very good action as regulators of insect growth.

The compounds of formula I are suitable for the control of insects of the families: Tettigonidae, Gryllidae, Blattidae, Reduviidae, Phyrrhocoridae, Cimicidae, Delphacidae, Aphididae, Diaspididae, Pseudococcidae, Scarabaeidae, Dermestidae, Coccinellidae, Tenebrionidae, Chrysomelidae, Bruchidae, Tineidae, Noctuidae, Lymatriidae, Pyrallidae, Culicidae, Tipulidae, Stomoxydae, Trypetidae, Muscidae, Calliphoridae and Pulicidae.

The insecticidal action can be substantially broadened and adapted to suit given circumstances by the addition of other insecticides and/or acaricides as well as insect bait substances. Suitable additives are, for example: organic phosphorus compounds, nitrophenols and derivatives thereof, pyrethrins, formamidines, ureas, carbamates, chlorinated hydrocarbons or other agents regulating the growth of insects.

The compounds of formula I can be used on their own or together with suitable carriers and/or additives. Suitable carriers and additives may be solid or liquid, and they correspond to the substances common in formulation practice, such as, for example, natural or regenerated substances, solvents, dispersing agents, wetting agents, adhesives, thickeners, binders and/or fertilisers.

For application, the compounds of formula I can be processed into the form of dusts, emulsion concentrates, granulates, dispersions, sprays or solutions, the formulation of these preparations being effected in a manner commonly known in practice.

The agents according to the invention are prepared in a manner known per se by the intimate mixing and/or grinding of active substances of formula I with suitable carriers, optionally with the addition of dispersing agents or solvents which are inert to the active substances. The active substances can be obtained and used in the following forms:

solid preparations: dusts, scattering agents, granulates, coated granulates, impregnated granulates and homogeneous granulates;

liquid preparations:
a. water-dispersible active-substance concentrates:
   wettable powders, pastes or emulsions;
b. solutions.

The content of active substance in the above described agents is between 0.1 and 95%; it is to be mentioned in this connection that in the case of application from an aeroplane, or by means of other suitable application devices, concentrations of up to 99.5%, or even the pure substance, can be employed.

The active substances of formula I can be formulated, for example, as follows:

Dusts

The following substances are used in the preparation of (a) a 5% dust, and (b) a 2% dust:
a.
5 parts of active substance,
95 parts of talcum;
b.
2 parts of active substance,
1 part of highly dispersed silicic acid,
97 parts of talcum.
The active substances are mixed and ground with the carriers.

Granulate

The following substances are used to prepare a 5% granulate:
5 parts of active substance,
0.25 part of epichlorohydrin,
0.25 part of cetyl polyglycol ether,
3.50 parts of polyethylene glycol,
91 parts of kaolin (particle size 0.3 - 0.8 mm).
The active substance is mixed with epichlorohydrin and dissolved with 6 parts of acetone; the polyethylene glycol and cetyl polyglycol ether are then added. The solution thus obtained is sprayed onto kaolin, and the acetone is subsequently evaporated off in vacuo.

Wettable powder

The following constituents are used for the preparation of (a) a 40%, (b) and (c) a 25%, and (d) a 10% wettable powder:
a.
40 parts of active substance,
5 parts of sodium lignin sulphonate,
1 part of sodium dibutyl-naphthalene sulphonate, 54 parts of silicic acid;
b.
25 parts of active substance,
4.5 parts of calcium lignin sulphonate,
1.9 parts of Champagne chalk/hydroxyethyl cellulose mixture (1:1),
1.5 parts of sodium dibutyl naphthalene sulphonate,
19.5 parts of silicic acid,
19.5 parts of Champagne chalk,
28.1 parts of kaolin;
c.
25 parts of active substance,
2.5 parts of isooctylphenoxy-polyoxyethylene-ethanol,
1.7 parts of Champagne chalk/hydroxyethyl cellulose mixture (1:1),
8.3 parts of sodium aluminium silicate,
16.5 parts of kieselguhr,
46 parts of kaolin;
d.
10 parts of active substance,
3 parts of a mixture of the sodium salts of saturated fatty alcohol sulphtes,
5 parts of naphthalenesulphonic acid/formaldehyde condensate,
82 parts of kaolin.

The active substances are intimately mixed, in suitable mixers, with the additives, and the mixture is then ground in the appropriate mills and rollers. Wettable powders are obtained which can be diluted with water to give suspensions of any desired concentration.

Emulsifiable concentrates

The following substances are used to prepare (a) a 10% and (b) a 25% emulsifiable concentrate:
a.
10 parts of active substance,
3.4 parts of epoxidised vegetable oil,
3.4 parts of a combination emulsifiers consisting of fatty alcohol polyglycol ether and aklylarylsulphonate calcium salt,
40 parts of dimethylformamide,
43.2 parts of xylene;
b.
25 parts of active substance,
2.5 parts of epoxidised vegetable oil,
10 parts of an alkylarylsulphonate/fatty alcohol polyglycol ether mixture,
5 parts of dimethylformamide
57.5 parts of xylene.

From these concentrates it is possible to prepare, by dilution with water, emulsions of any desired concentration.

Spray

The following constituents are used to prepare a 5% spray:
5 parts of active substance,
1 part of epichlorhydrin,
94 parts of ligroin (boiling limits 160° – 190° C).

EXAMPLE 1

A. Preparation of 4-[(4-phenoxy)-phenoxy]-butyric acid diethylamide 17 g of potassium-tert.-butanolate is added at 10° C to a solution of 28 g of 4-phenoxy-phenol in 100 ml of anhydrous dimethylsulphoxide. After the base has completely dissolved, an addition is made dropwise in the course of 2 hours, with stirring, of 26.5 g of chlorobutyric acid diethylamide dissolved in 20 ml of dimethylsulphoxide and the whole is further stirred overnight at room temperature. For further processing, the reaction mixture is poured into ice water, and extraction is repeatedly performed with diethyl ether. The combined ether phases are washed four times with cold 10% potassium hydroxide solution and subsequently repeatedly with water; they are then dried by means of sodium sulphate. After the ether has been distilled off, there is obtained crude 4-[(4-phenoxy)-phenoxy]-butyric acid diethylamide, which is purified by chromatography on silica gel (eluant: ether/hexane 1:3), and recrystallised from isopropanol/hexane, M.P. 73°–74° C.

B. Preparation of 4-[(4-phenoxy)-phenoxy]-3-methyl-butenic acid ethyl ester 15.6 g of 4-[(4-phenoxy)-phenoxy]-3-methyl-2-butenic acid ethyl ester, dissolved in 200 ml of ethyl acetate, is, after the addition of 4 g of palladium catalyst (content 5% Pd), catalytically hydrogenated at room temperature, with 1125 ml of hydrogen being absorbed within about 22 hours.

The hydrogenation solution is thereupon filtered off from the catalyst, the solvent is completely removed in vacuo, and the oily residue is chromatographically purified on silica gel (eluant: ether/hexane 1:5). There is obtained the compound of the formula

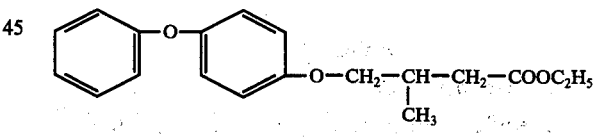

having a refractive index of $n_D^{20}$: 1.5383.

The following compounds are obtained in an analogous manner:

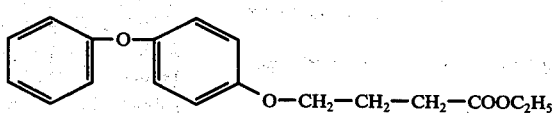

$n_D^{20}$: 1,5440

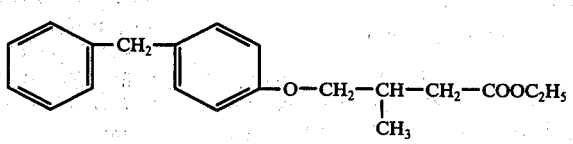

$n_D^{20}$: 1,5372

-continued

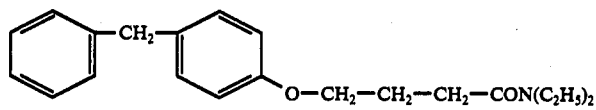 $n_D^{20}$: 1,5532

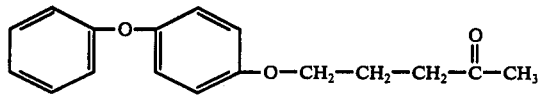 $n_D^{20}$: 1,5598

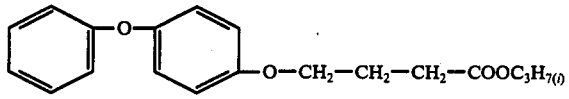 $n_D^{20}$: 1,5359

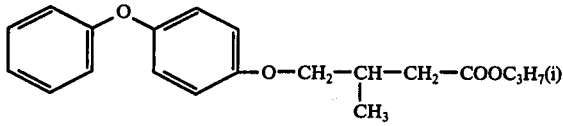 $n_D^{20}$: 1,5320

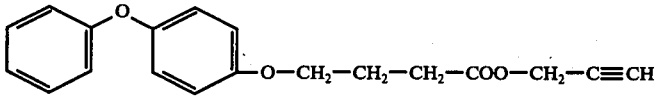 $n_D^{20}$: 1,5553

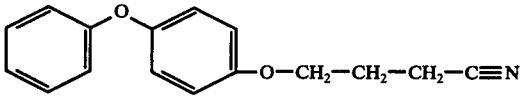 M.P.: 39–40° C

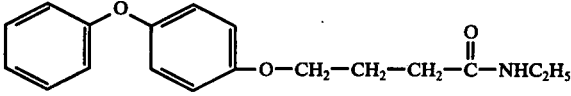 M.P.: 72–73° C

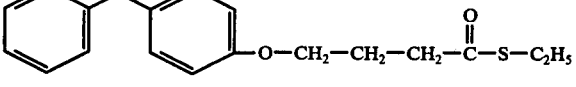 $n_D^{20}$: 1,5742

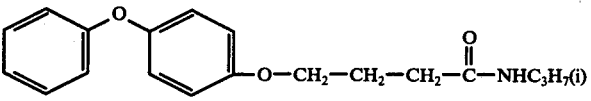

EXAMPLE 2

Contact action on Dysdercus-fasciatus larvae

A specific amount of a 0.1% acetonic active-substance solution (corresponding to 10 mg of active substance per square meter) was transferred by pipet to an aluminium dish and uniformly distributed. After evaporation of the acetone, 10 larvae in the 5th stage of Dysdercus fasciatus were placed into the treated dish containing feed and moist cotton wool. The dish was then covered with a perforated lid. After about 10 days, i.e. as soon as the control insects had moulted into adults, the test insects were examined to determine the nunber of normal adults.

Compounds according to Example 1 exhibited a good action in the above test.

EXAMPLE 3

Contact action of Aedes-aegypti larvae

About 20 two-day-old larvae of the yellow-fever mosquito (Aedes aegypti) were placed in position in a beaker containing a solution of the active substance (concentration 5 ppm). The beaker was then covered with a perforated lid. After the control insects had moulted into adults, the test insects were examined and the percentage of normal adults in comparison with the control adults determined.

Compounds according to Example 1 exhibited a good action in the above test.

EXAMPLE 4

Contact action on Tenebrio-molitor pupae

A specific amount of a 0.1% acetonic active-substance solution corresponding to 10 mg of active substance per square meter was transferred by pipet into an aluminium dish and uniformly distributed. Afte evaporation of the acetone, 10 freshly formed pupae were placed on the treated surface, and the dish was covered with a perforated lid. After the control insects had left the cocoon as imagines, the test insects were examined to determine the number of normal adults.

Compounds according to Example 1 exhibited a good action in the above test.

I claim:

1. A compound of the formula

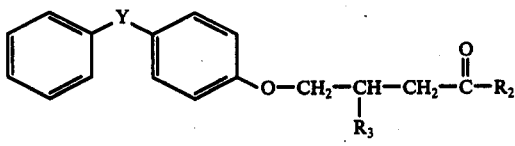

wherein
  $R_2$ represents methoxy, ethoxy, n-propoxy, isopropoxy, n-butoxy, isobutoxy, sec.butoxy, tert.butoxy or propargyloxy,
  $R_3$ represents hydrogen or methyl, and
  Y represents methylene or oxygen.

2. A compound according to claim 1 wherein $R_2$ represents methoxy, ethoxy or isopropoxy.

3. 4-[(4-Phenoxy)-phenoxy]-3-methyl-butyric acid isopropyl ester according to claim 2.

4. 4-[(4-Phenoxy)-phenoxy-]-3-methyl-butyric acid ethyl ester according to claim 2.

5. 4-[(4-Phenoxy)-phenoxy]-butyric acid ethyl ester according to claim 2.

6. An insecticidal composition comprising (1) an insecticidally effective amount of a compound according to claim 1 and (2) a carrier.

7. A method for combatting insects which comprises applying thereto an insecticidally effective amount of a compound according to claim 1.

8. A method according to claim 7 in which $R_2$ is methoxy, ethoxy or isopropoxy.

9. A method according to claim 8 in which the compound is 4-[(4-phenoxy)-phenoxy]-3-methylbutyric acid isopropyl ester.

10. A method according to claim 8 in which the compound is 4-[(4-phenoxy)-phenoxy]-3-methylbutyric acid ethyl ester.

11. A method according to claim 8 in which the compound is 4-[(4-phenoxy)-phenoxy]-butyric acid ethyl ester.